United States Patent [19]
Armbruster et al.

[11] Patent Number: 5,269,762
[45] Date of Patent: Dec. 14, 1993

[54] PORTABLE HAND-HELD POWER ASSISTER DEVICE

[75] Inventors: Randy E. Armbruster; Peter Affolter, both of Rochester, N.Y.

[73] Assignee: Sterling Winthrop, Inc., New York, N.Y.

[21] Appl. No.: 871,879

[22] Filed: Apr. 21, 1992

[51] Int. Cl.$^5$ ............................................. A61M 37/00
[52] U.S. Cl. .................................. 604/155; 604/131
[58] Field of Search .............. 604/155, 154, 150, 131, 604/152, 143, 147, 136, 137

[56] References Cited

U.S. PATENT DOCUMENTS

| | | |
|---|---|---|
| 3,623,474 | 11/1971 | Heilman et al. . |
| 3,701,345 | 10/1972 | Heilman et al. . |
| 3,858,581 | 1/1975 | Kamen .................. 604/155 |
| 4,006,736 | 2/1977 | Kranys et al. . |
| 4,108,177 | 8/1978 | Pistor .................... 604/155 |
| 4,191,187 | 3/1980 | Wright .................. 604/155 |
| 4,273,122 | 6/1981 | Whitney et al. . |
| 4,326,517 | 4/1982 | Whitney et al. ..... 604/155 |
| 4,426,024 | 1/1984 | Hogan et al. ........ 604/141 |
| 4,435,173 | 3/1984 | Siposs et al. ........ 604/155 |
| 4,519,258 | 5/1985 | Jakubowicz . |
| 4,544,369 | 10/1985 | Skakoon et al. . |
| 4,668,220 | 5/1987 | Hawrylenko . |
| 4,676,781 | 6/1987 | Phillips et al. ...... 604/136 |
| 4,677,980 | 7/1987 | Reilly et al. . |
| 4,695,271 | 9/1987 | Goethel . |
| 4,931,041 | 6/1990 | Faeser ................... 604/155 |
| 4,950,246 | 8/1990 | Muller . |
| 4,976,696 | 12/1990 | Sanderson et al. . |
| 5,034,003 | 7/1991 | Denance .............. 604/155 |
| 5,139,484 | 8/1992 | Hazon et al. ........ 604/155 |
| 5,176,645 | 1/1993 | Guerrero ............. 604/150 |

Primary Examiner—Paul J. Hirsch
Attorney, Agent, or Firm—Imre (Jim) Balogh; Arthur Rosenstein

[57] ABSTRACT

A hand-held power injection device is provided for injecting liquid, such as contrast media, into the vascular system of a mammal. The device comprises a pistol-shaped housing which encloses a battery-powered D.C. motor for constant-rate delivery of liquid from a syringe.

9 Claims, 4 Drawing Sheets

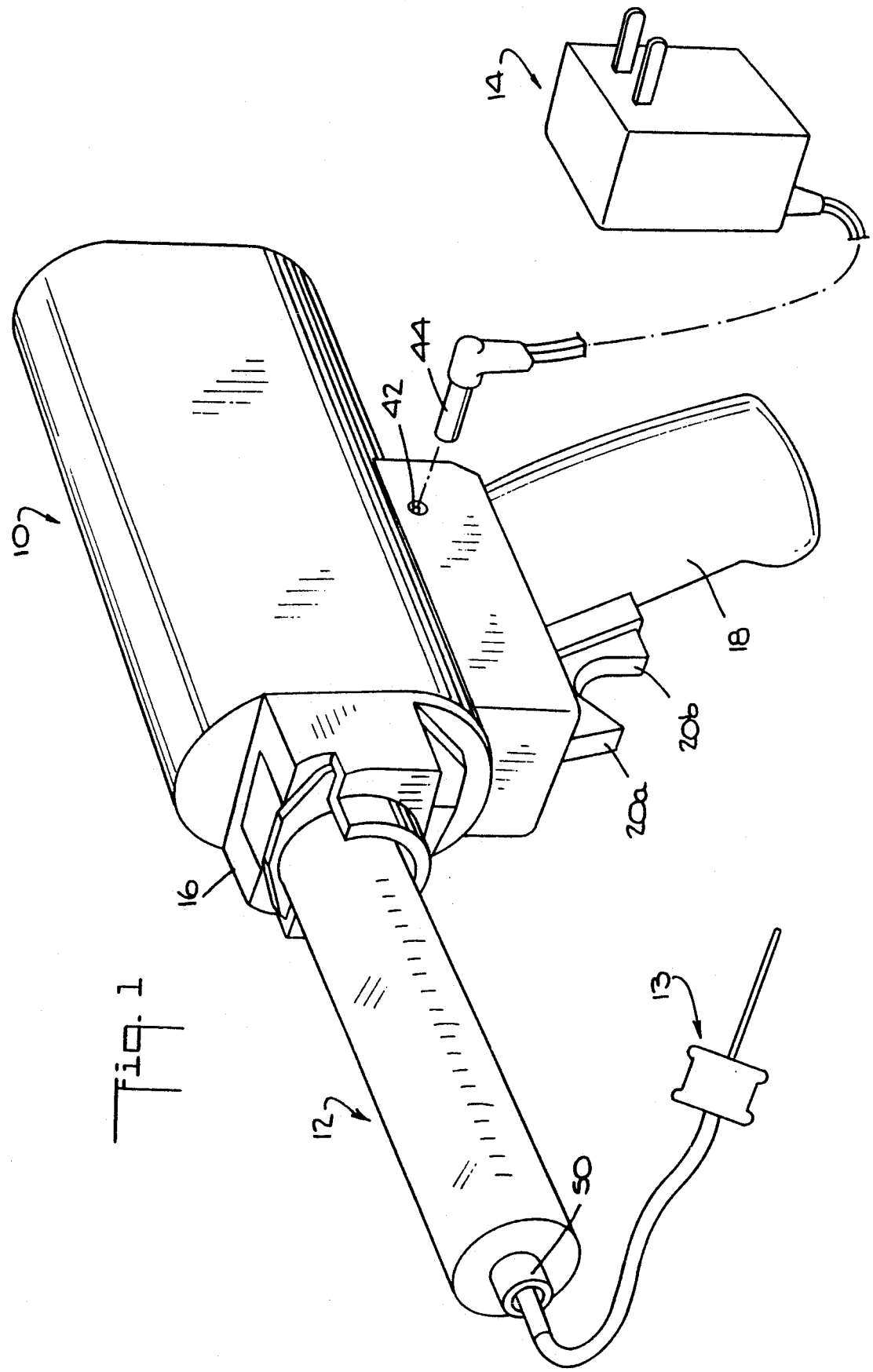

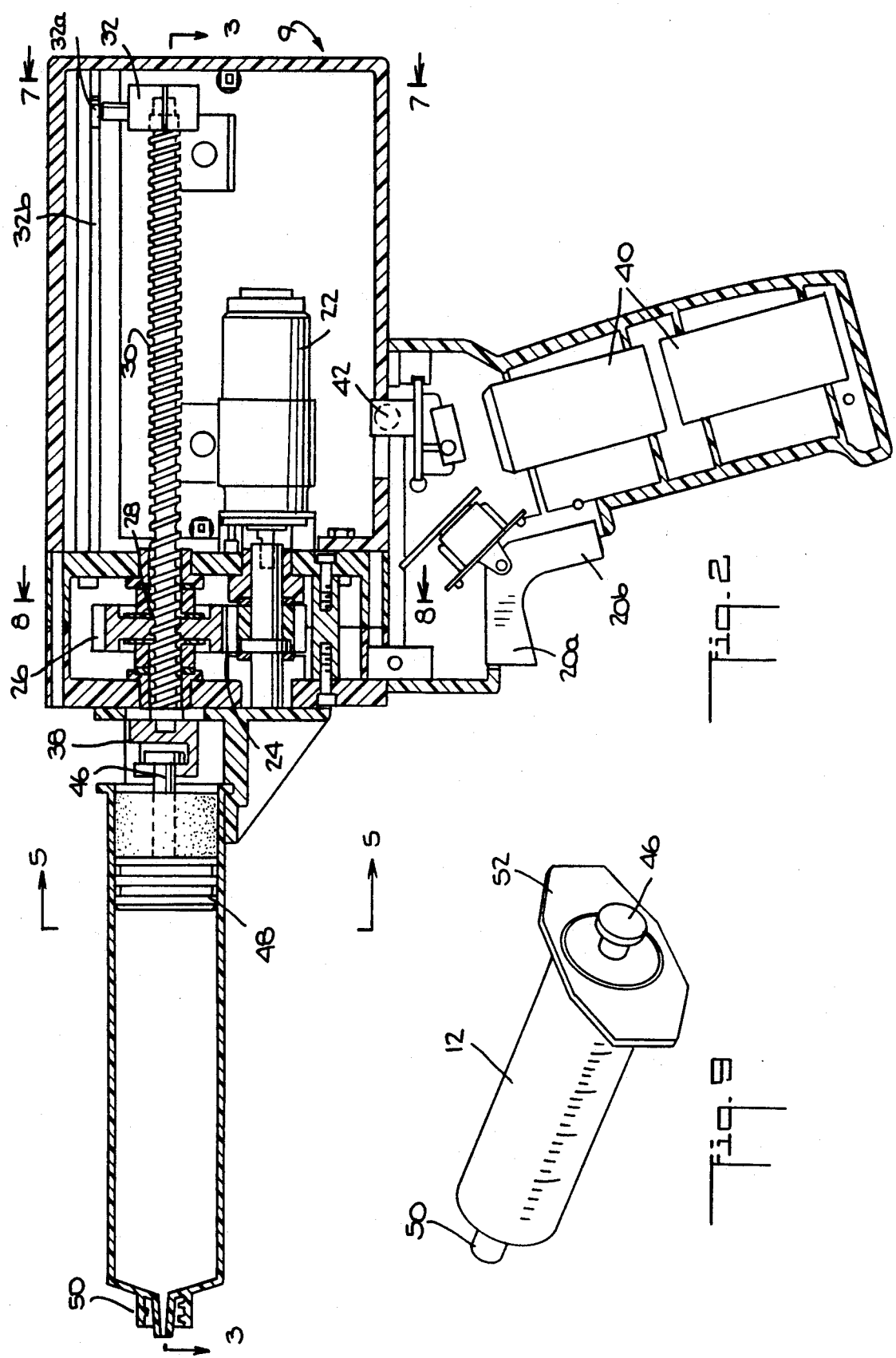

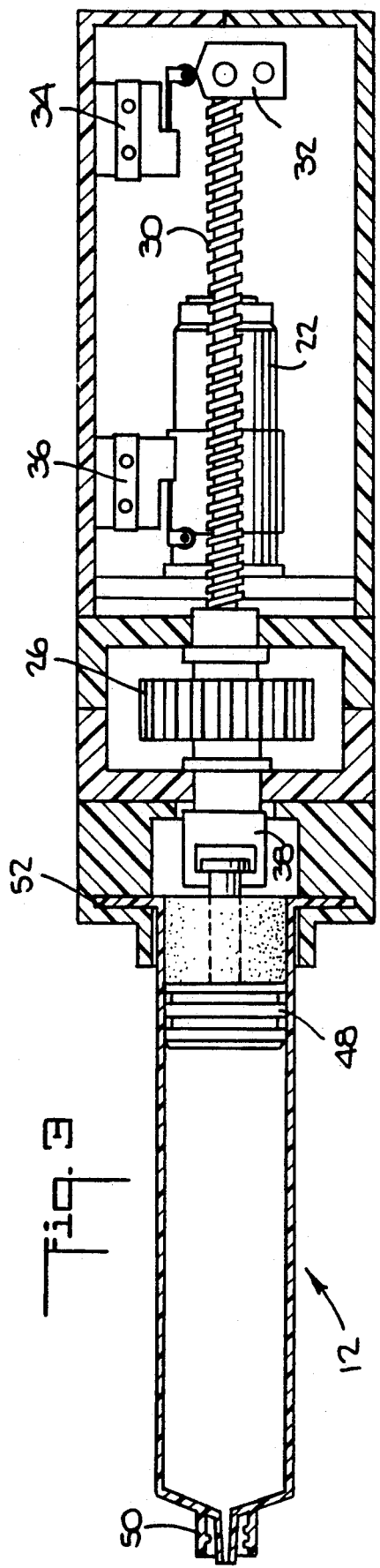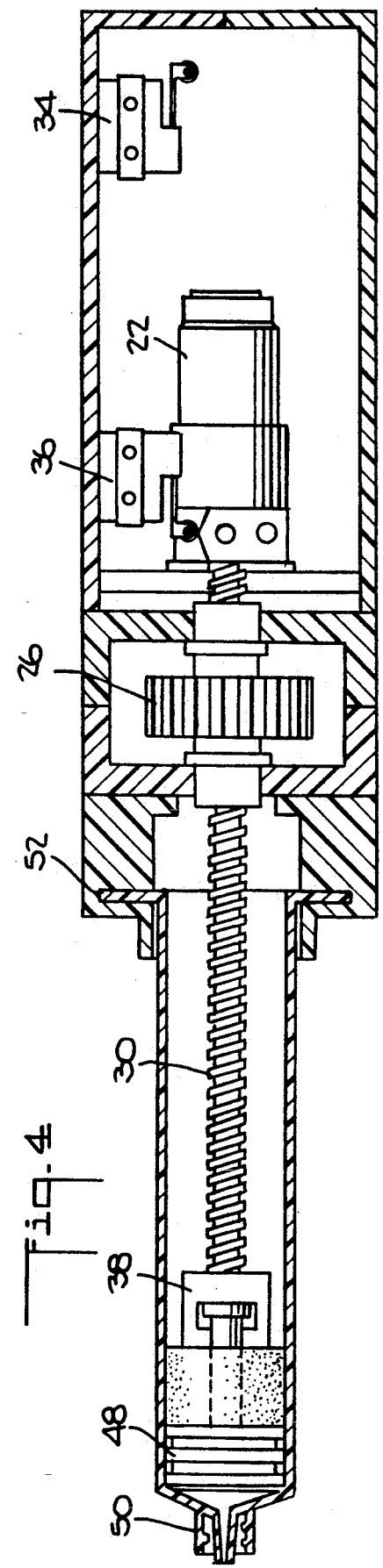

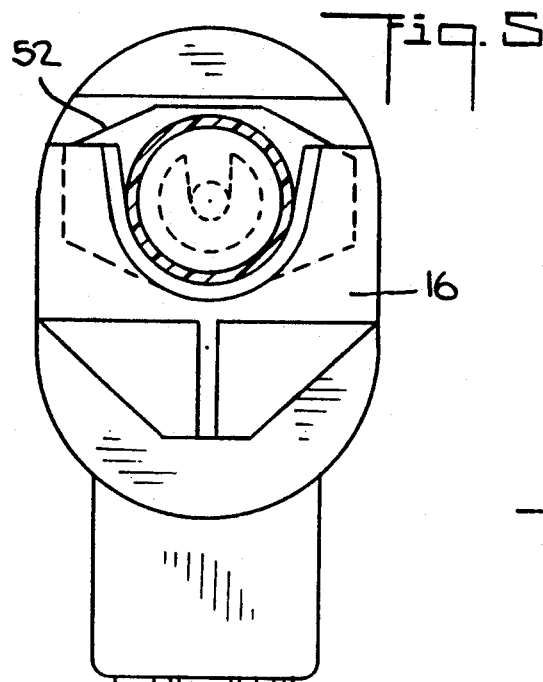
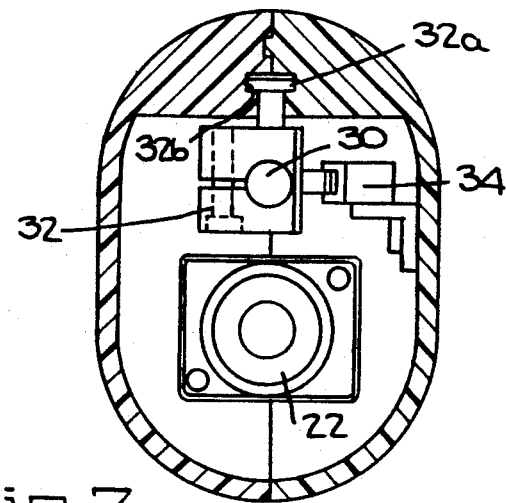
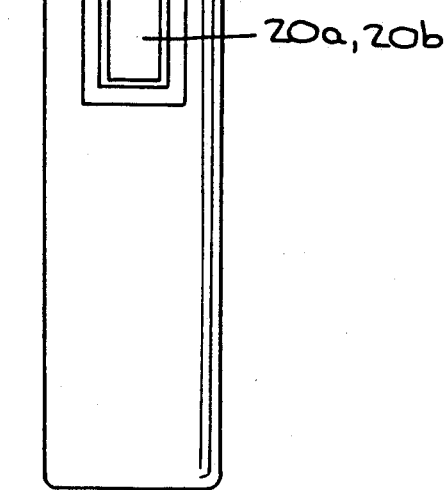
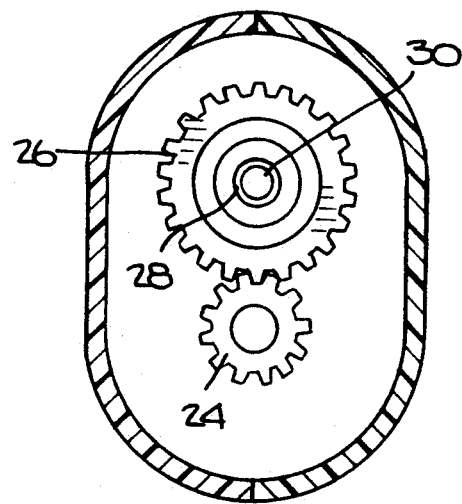
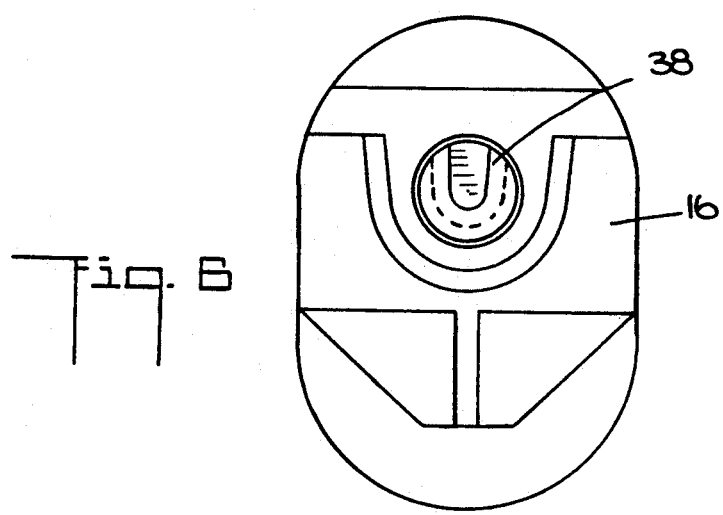

PORTABLE HAND-HELD POWER ASSISTER DEVICE

BACKGROUND OF THE INVENTION

1. Field of the Invention

This invention relates to a hand-held controllable power assister device as applied to syringes adopted to deliver a liquid into a patient. More particularly, the invention relates to a held-held controllable power injection device for delivering, by injection, x-ray contrast media into a patient prior to or during urographic or angiographic procedures.

2. Reported Developments

Urography is a radiological technique wherein at least a part of the urinary tract of a mammal is rendered opaque by intravenous injection of a contrast medium or by injection into the bladder through the urethra.

Angiography is also a radiological technique wherein the arteries or veins of a mammal are outlined by injecting a radiographic medium.

In both techniques the coated vascular structures are radiographically imaged for diagnostic purposes.

For delivery to the desired site, the contrast medium is placed in an appropriate syringe and forced through a hollow needle or a catheter in such a manner that the contrast medium enters the blood stream or the bladder at the appropriate time and place for taking radiographic images. As contrast medium is being injected to the site to be visualized through the hollow needle or a catheter, high pressures are often encountered, sometimes as high as 1,000 psi. This requires a rather high force to be exerted on the piston in order to deliver the content of the syringe. Furthermore, such force is to be exerted in a constant manner for continuous and even volume delivery of the contrast medium. Early injection systems were designed for manual injection of the contrast medium by means of a hand-held glass syringe. A mechanical injection system activated by a foot switch has also been, and is still being used for most general radiographic procedures. However, this system was only rarely used for coronary angiography for the probable reason that operator control is greatly reduced and the risk of coronary artery dissection increased.

Power injectors in general have certain advantages over hand-operated injectors including the following. They reduce reliance on an assistant enabling the operator to be in complete control of the injection of the contrast medium, they can deliver a precise volume, and the pressure generated can be limited by presetting a pressure limit.

Power injectors are of three types: hydraulic, pneumatic and electric. Hydraulic injectors have an electric motor connected to a hydraulic pump, which drives a ram connected to a syringe that contains the contrast medium. In pneumatic injectors, the source of power is compressed gas supplied by a tank or compressor. Electric injectors are powered by electric motors in which a transmission means serves to change circular motion into linear motion which then drives a ram.

While typical power injectors eliminate the physical effort required with manual injectors, they are not easy to use, are expensive and the perception of instantaneous control present with manual injectors is lost because the syringe and controls for the injectors are not hand-held or not conveniently handleable during the injection process. For example, a gas power-assister hand-held syringe does eliminate the physical effort associated with manual injection and also provides a perceived instantaneous control of the injection, however, it requires a gas system to power the syringe, such as pressurized carbon dioxide gas. The gas delivery system includes a carbon dioxide gas tank with various indicators and controls, which reduces the portability of the device, it requires valuable space in the proximity of the injection, it adds to the complexity of using the device for the intended purpose and requires periodic replacement of the gas tank.

Battery powdered injectors are also available for use in angiography and urography employing a syringe for holding a contrast medium and a plunger connected to a mechanical means to automatically deliver the contrast medium. Some of these injectors include microprocessor technology for programming rates and time delivery and have visual or audio display for ease of controlling the injection process. As these injectors become more sophisticated, the cost of making and using them increases as well as the complexity of use tends to increase the opportunities for breakdown.

The present invention is directed to a hand-held, light-weight power assister which eliminates the physical effort required with manual injectors but otherwise allows the practitioner complete human control of the injection process.

SUMMARY OF THE INVENTION

The power assister device of the present invention is designed to be hand-held by one hand, light weight, inexpensive and to allow complete control over the process of delivering radiopaque media to the patient by the medical practitioner. To that end, its configuration resembles a pistol the handle portion of which provides for firm hold. Activating switch, having on-off— and neutral positions, is located in the handle portion to be controlled by the index finger of the practitioner. While the device does not incorporate complicated and expensive electronic components which tend to break down and are cumbersome to use, it provides electrical energy to deliver the contrast media to the patient at a constant rate of delivery and it incorporates limit switches to automatically stop the electric motor when the lead screw, which engages the piston, is in its initial or completely extended position.

In accordance with the invention, the hand-held power assister device comprises:

a pistol-shaped casing;
a syringe; and
recharging means.

The casing is made of light but tough plastic material and safely houses all components therein which include:

a D. C. motor to provide angular motion;
rechargeable batteries to supply electrical power to the motor;
recharging means for the batteries;
a lead screw having a female engagement means to engage a piston;
gear means to translate angular motion produced by the motor to linear motion of the lead screw;
limit switches to stop the motor when lead screw is in its initial or completely extended positions; and
trigger switch with electrical leads to batteries and to the motor for controlling the movement of the lead screw.

The syringe used in the present invention may be of various sizes, such as from 10 ml to 50 ml to 100 ml or larger, depending on the volume requirement of the patient and the type and concentration of the radiopaque or other media. The syringe has a luer connector at one end to engage a catheter or a butterfly needle which is to be inserted in the injection site. The other end of the syringe is equipped with a flange to engage a receiving slot in the front end of the casing of the handheld power assister device. The syringe barrel holds a slideable piston or plunger therein and is equipped with a male engagement means to mate with female engagement means of the lead screw.

The recharging means consists of a recharger unit equipped with two plugs one of which is inserted into the receptacle on the power assister device and the other into a standard electrical outlet.

BRIEF DESCRIPTION OF THE DRAWINGS

FIG. 1 is a perspective view of the hand-held power assister, a syringe engaged with said power assister, butterfly needle in place and battery charger unit;

FIG. 2 is a sectional view of the hand-held power assister;

FIG. 3 is a cross-sectional view of the hand-held power assister taken along the line 3—3 of FIG. 2, showing the syringe engaged and the syringe piston in its engagement position.

FIG. 4 is a cross-sectional view of the hand-held power assister, showing syringe piston in its extended position, taken along line 3—3 of FIG. 2;

FIG. 5 is a transverse cross-sectional view of the hand-held power assister and syringe engaged therewith, taken along line 5—5 of FIG. 2;

FIG. 6 is a partial transverse cross-sectional view of the hand-held assister device taken along line 5—5 of FIG. 2;

FIG. 7 is a cross-sectional view of the hand-held power assister taken along the line 7—7 of FIG. 2;

FIG. 8 is a cross-sectional view of the hand-held power assister taken along the line 8—8 of FIG. 2; and FIG. 9 is a perspective view of the syringe not engaged with the power assister.

DESCRIPTION OF THE PREFERRED EMBODIMENT

Referring to FIG. 1, power assister device 10 is shown with syringe 12 engaging said device, butterfly needle 13 attached to said syringe by luer connector 50 and battery recharger 14 is ready to engage power assister device 10 by insertion of plug 44 into receptacle 42.

When assembled together, power assister device 10 and syringe 12, along with handle 18 and trigger 20a-20b, resemble a pistol. This configuration provides for firm hold control and convenient handleability. The power assister device 10 comprises a casing which serves as a housing and chassis for the components contained therein.

Referring to syringe 12, as shown in FIGS. 1, 2, 3 and 9, it comprises: a syringe barrel to receive an injectable agent therein, said syringe barrel having a luer connector 50 at one end thereof serving as means for attaching butterfly needle 13 thereto, and the other end of said tubular body having male coupling 46 to engage female coupling 38. Flange 52 of syringe 12 locates and fixes syringe within a complimentary slot (not shown) in front 16 of the power assister device 10. Loading of syringe 12 is exceptionally easy and practical, since the syringe is drop-loaded onto said slot without the need of any twisting or turning motion. Positioned in said syringe barrel in a slideable relationship is piston 48 integral with male coupling 46.

As best seen in FIGS. 2, 3, 7 and 8, the casing or housing of the power assister device 10 houses a D. C. motor 22 which produces angular rotation of gear 24. Gear 24 drives gear 26 which has internal thread 28. Linear movement of lead screw 30 is produced by preventing its rotation and by the angular rotation of internal thread 28. A follower 32, fixed to the back end of lead screw 30, prevents rotation of the lead screw during linear movement by the engagement of peg 32a of the follower 32 rolling or sliding in slot 32b.

D. C. motor 22 is powered by rechargeable batteries 40, which are located in handle 18 of power assister device 10. Trigger switch 20a-20b engageably coupled to batteries 40 and D.C. motor 22 has three positions: forward drive, reverse drive and off position. Forward limit switch 36 is positioned so that lead screw follower 32 triggers the switch and stops the motor when piston 48 is in its extended position as shown in FIG. 4. Likewise, the backwards limit switch 34 is positioned so that the lead screw follower 32 triggers the switch and stops the motor 22 when piston 48 is in its engagement position as shown in FIG. 3.

The power assister device 10 is recharged by plugging recharger 14 in a standard electrical outlet and inserting plug 44 into receptacle 42 during periods in which the device is not in use.

Reference is now made to the operation of the hand-held power assister. The syringe 12 could be prefilled with an injectable liquid, such as contrast media, or the power assister device 10 could be used to fill the syringe. If not prefilled, the empty syringe 12 is loaded onto the front 16 of the device, having male coupling 46 engage female couple 38, then placing the power assister device 10 in an upright position by placing it with is flat surface 9 on top of a flat object, such as a table. The syringe 12 is then filled with contrast media by first driving the piston 48 to its extended position within the syringe as shown in FIG. 4. A plastic tube (not shown) is attached to luer connector 50 and the contrast media is syphoned into the syringe 12 by placing the opposite end of the plastic tube in a container filled with contrast media and retracting piston 48 back into its engagement position. Upon completion of the process the plastic tube is removed from the luer connector 50 and a butterfly needle 13 is attached thereto. After butterfly needle 13 is attached to luer connector 50, the upright position of power assister device 10 is maintained until the air from syringe 12 and butterfly needle 13 is purged by driving piston 48 in the forward direction. To drive piston 48 forward or in reverse trigger switch 20a-20b is provided. Trigger switch 20a-20b is positioned in handle 18 of the power assister device 10 to control both the forward and reverse motion of the piston: pressing 20b results in forward motion of piston 48, while pressing 20a results in reverse motion thereof. When neither 20a nor 20b trigger switch is pressed, switch automatically reverts to neutral or off position and motor 22 becomes disengaged.

In the case when the syringe 12 is prefilled with contrast media, the syringe is loaded in the same manner as above-described, then the power assister 10 is positioned in an upright position. Syringe cap (not shown) is removed from luer connector 50 and butterfly needle 13 is attached to luer connector 50. The air is then purged from the syringe as above-described.

Upon purging the air from syringe 12, the power assister device 10 is held by the medical practitioner at handle 18 with index finger resting on trigger switch 20a-20b which is in the off position. Protective sheath (not shown) is removed from butterfly needle 13 and the same is inserted into the injection sight on the patient. The practitioner then activates motor 22 by pressing trigger switch 20b which electrically engages batteries 40 with motor 22. Motor 22 produces angular motion which is converted into linear motion through gears 24 and 26 acting on lead screw 30. Lead screw 30 drives piston 48 in the barrel of syringe 12 forcing contrast media through butterfly needle into the injection sight. Piston 48 is driven by lead screw 30 at a steady rate, while the practitioner is able to visually observe the expulsion of the contrast media from syringe 12. The medical practitioner is in complete control of the injection process. Unlike with very expensive and complicated devices where electronics take complete control over the process with the exclusion of the medical practitioner, the instant power assister device accomplishes one result: responds to the desire of the practitioner by forcing the contrast media out of syringe 12 into the patient at a steady rate of delivery. The injection process may be interrupted any time upon releasing trigger switch into neutral position. When lead screw 30 is in its completely extended position, that is, piston 48 has completely discharged contrast media from syringe 12, lead screw follower 32 triggers forward limit switch 36 to stop motor 22.

Upon completing the injection process, butterfly needle 13 is disconnected from the patient and lead screw 30 is retracted to its initial engagement position. Syringe 12 is disconnected from power assister device 10 by disengaging male coupling 46 from female coupling 38 and disengaging flange 52 from receiving slot on front portion 16 of the device 10.

As is apparent from the foregoing description, the power assister device of the present invention is extremely simple, compact, easy to hold and operate and is inexpensive. The lack of complicated electronic components virtually eliminates failures and breakdowns which plague complicated instruments. Medical personnel have complete control during the use of the device which makes the practice of delivering contrast media to the patient a more tolerable and pleasant experience than that associated with bulky, complicated instrumentalities.

What is claimed is:

1. A hand-held power injection device for injecting contrast media into the vascular system of a mammal said device comprising:
   a pistol-shaped casing to provide for ease of handling, said casing having a main tubular body portion and a handle portion integral therewith to house and support component parts therein;
   a syringe receiving means in said tubular body portion;
   a syringe engaging said tubular body portion and containing a piston therein having a male coupling means;
   a motor capable of generating angular motion, located in said tubular body portion;
   rechargeable batteries located in said handle portion for energizing said motor;
   a lead screw, having a female coupling means to mate with said male coupling means of said syringe, said lead screw rotatably coupled with said motor by gear means which convert angular motion to linear motion;
   limit switches connected to said lead screw and motor to automatically stop said lead screw when it is in the initial or completely extended position; and
   a trigger switch connected to said motor and said batteries to control movement of said lead screw coupled to said piston to inject contrast media into the vascular system of a mammal.

2. A hand-held power injection device for delivering liquid media to a patient comprising:
   a pistol-shaped casing to provide for ease of handling, said casing comprising a main tubular body portion having a distal end and a proximal end and a handle portion integral therewith at the proximal end thereof to house and support component parts therein;
   a syringe removably coupled to said distal end of said main tubular body portion of said pistol-shaped casing; and a trigger switch in said handle portion of said pistol-shaped casing; said pistol-shaped casing containing drive means which comprises:
   a battery powered motor to generate angular rotation;
   a lead screw rotatably coupled with said motor by gear means to convert angular rotation to linear motion, said lead screw having at one end thereof a female coupling means;
   a first limit switch connected to said lead screw and said motor to automatically disengage said motor and prevent further forward driving of the lead screw when the lead screw is at its completely extended position;
   a second limit switch connected to said lead screw and motor to automatically disengage said motor and to prevent further reverse driving of the lead screw when the lead screw is at its initial position;
   said syringe comprises:
   a syringe barrel having a leur connector at one end thereof for receiving a catheter and a flange at the other end thereof for drop-load engaging said tubular body portion of said casing and a piston slideably positioned in said syringe barrel having a male coupling means to engage said female coupling means of said lead screw;
   said trigger switch connected to said motor and said battery having forward, reverse and off positions to control movement of said lead screw coupled to said piston to inject liquid media into a patient.

3. The hand-held power injection device of claim 2 wherein said liquid media contains an imaging agent.

4. The hand-held power injection device of claim 3 wherein said imaging agent is for angiographic examination of a mammal.

5. The hand-held power injection device of claim 3 wherein said imaging agent is for urographic examination of a mammal.

6. A method of delivering a liquid medium into the vascular system of a mammal using a power injection device comprising:
   a pistol-shaped casing to provide for ease of handling, said casing comprising a main tubular body portion having a distal end and a proximal end and a handle portion integral therewith at the proximal end thereof to house and support component parts therein;

a syringe removably coupled to said distal end of said main tubular body portion of said pistol-shaped casing; and a trigger switch in said handle portion of said pistol-shaped casing; said pistol-shaped casing containing drive means which comprises:

a battery powered motor to generate angular rotation;

a lead screw rotatably coupled with said motor by gear means to convert angular rotation to linear motion, said lead screw having at one end thereof a female coupling means;

a first limit switch connected to said lead screw and said motor to automatically disengage said motor and prevent further forward driving of the lead screw when the lead screw is at its completely extended position;

a second limit switch connected to said lead screw and motor to automatically disengage said motor and prevent further reverse driving of the lead screw when the lead screw is at its initial position;

said syringe comprises:

a syringe barrel having a leur connector at one end thereof for receiving a catheter and a flange at the other end thereof for drop-load engaging said tubular body portion of said casing and a piston slideably positioned in said syringe barrel having a male coupling means to engage said female coupling means of said lead screw;

said trigger switch connected to said motor and said battery having forward, reverse and off positions to control movement of said lead screw coupled to said piston to inject liquid media into a patient;

said method comprises the steps of:

(a) syphoning said liquid medium into said syringe through a tubing means attached to said leur connector at one end thereof and placing said tubing means into said liquid medium at the opposite end thereof and activating the trigger switch at its reverse position to retract said piston into its engagement position;

(b) replacing said tubing means with a catheter;

(c) inserting said catheter into the vascular system of said mmammal;

(d) pressing said trigger switch at its forward position to deliver said liquid medium into said mammal at a constant rate of delivery.

7. The method of claim 6 wherein said liquid medium comprises an imaging contrast agent.

8. The method of claim 7 wherein said imaging contrast agent is for angiographic examination of said mammal.

9. The method of claim 7 wherein said imaging agent is for urographic examination of said mammal.

* * * * *